United States Patent [19]

Shafer

[11] 4,444,199

[45] Apr. 24, 1984

[54] METHOD AND APPARATUS FOR MONITORING PHYSIOLOGICAL CHARACTERISTICS OF A SUBJECT

[75] Inventor: William A. Shafer, 1745 Soledad Way, San Diego, Calif. 92109

[73] Assignees: William A. Shafer; Decision Science, Inc., both of San Diego, Calif.

[21] Appl. No.: 287,073

[22] Filed: Jul. 21, 1981

[51] Int. Cl.³ .............................................. A61N 5/04
[52] U.S. Cl. .................................................. 128/691
[58] Field of Search ............... 128/653, 693, 727, 723, 128/734, 774, 782, 691

[56] References Cited

U.S. PATENT DOCUMENTS

| | | |
|---|---|---|
| 3,587,562 | 6/1971 | Williams .............................. 128/723 |
| 3,855,416 | 12/1974 | Fuller . |
| 3,855,417 | 12/1974 | Fuller . |
| 3,855,418 | 12/1974 | Fuller . |
| 3,926,177 | 12/1975 | Hardway, Jr. et al. ............. 128/722 |
| 3,971,034 | 7/1976 | Bell et al. . |
| 4,056,097 | 11/1977 | Maass . |
| 4,093,821 | 6/1978 | Williamson . |
| 4,142,067 | 2/1979 | Williamson . |
| 4,320,766 | 3/1982 | Alihanka et al. .................... 128/782 |
| 4,328,809 | 5/1982 | Hirschowitz et al. ............... 128/653 |

OTHER PUBLICATIONS

Lonsdale et al., "Procedings of the 9th Annual Rocky Mountain Bioengineering Symposium & 10th International ISA Biomedical Sciences Instrumentation Symposium", Omaha, Nebraska, May 1-3, 1972, vol. 9, pp. 139-143.

Primary Examiner—William E. Kamm
Attorney, Agent, or Firm—Spencer & Frank

[57] ABSTRACT

A method and apparatus for monitoring physiological changes in a subject wherein the method comprises the steps of placing a sensor adjacent to and spaced from the body of the subject, filtering the signal to separate frequency components lower than 4 Hz, amplifying the generated signal and displaying the amplified signal which is indicative of changes in the physiological characteristics of the subject. The apparatus senses the electromagnetic radiation emitted as generated by physiological processes and reaction to stress, and provides this information as a composite of heart rate, respiration rate, pulse amplitude and respiratory excursion. It can also be used to indicate the comparative circulation in different parts of the body, the circulation delay time and to provide information relating to the autonomic nervous response. The sensor may be placed within a bed, seat cushion or head rest so that the subject's physiological response can be measured without his being disturbed by the sensor.

7 Claims, 11 Drawing Figures

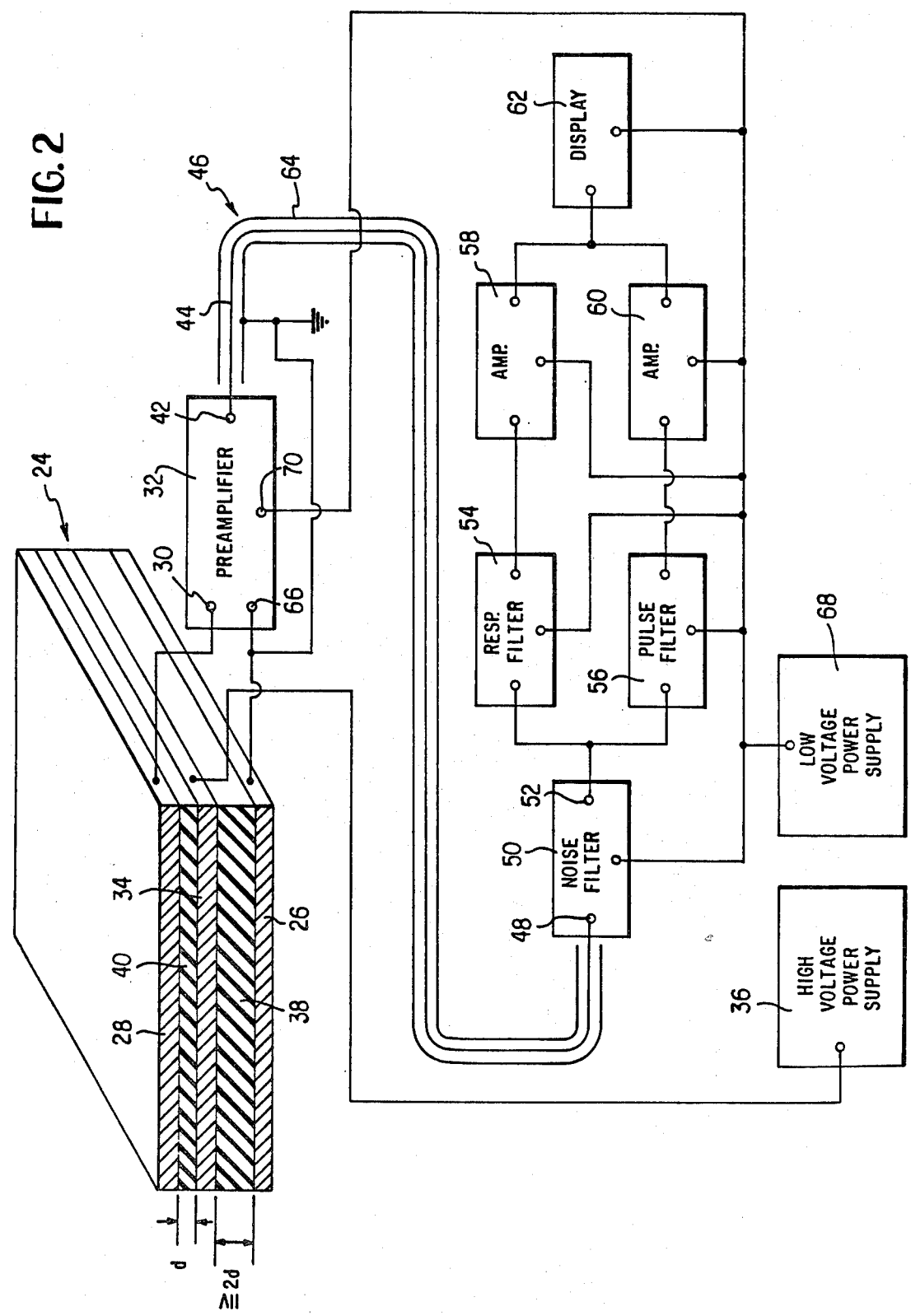

METHOD AND APPARATUS FOR MONITORING PHYSIOLOGICAL CHARACTERISTICS OF A SUBJECT

BACKGROUND OF THE INVENTION

This invention relates to a method and apparatus for monitoring the physiological characteristics of a subject. In particular, it relates to a method and apparatus for detecting changes in the body's cardiovascular and respiratory systems innervated by the autonomic nervous system without requiring the attachment of sensors to the body of the person being examined.

Instrumentation is available for detecting and measuring relatively small changes in brain wave patterns, heart activity, skin conductivity, breathing activity and other physiological properties. However, in general, such devices have the disadvantage that sensors must be attached to the body of the subject being tested. In the case of burn victims, it is desirable to have a continuous record of vital signs, but electrodes often cannot be placed on the skin. In other situations, such as when persons are undergoing intensive medical care, suffering mental distress, exhibiting unreasonable behavior, working in a high-stress environment or require monitoring for long periods of time for any reason, the reaction of the subject to the attachment of sensors to his body can affect the measurements to such an extent that the validity of the evaluation is substantially reduced.

Accordingly, it is an object of the invention to provide a method and apparatus for monitoring physiological changes in a subject without attaching wires or other devices to his body.

Another object is to permit monitoring a subject under conditions in which he is not aware he is being examined.

Still another object is to provide apparatus for physiological monitoring that is relatively simple to use and inexpensive to manufacture.

SUMMARY OF THE INVENTION

The invention comprises a method for monitoring physiological changes in a subject which comprises the steps of placing a flat, flexible antenna or sensor adjacent to and spaced from the body of the subject, filtering the signal to frequency components no higher than 4 HZ, amplifying the generated signal and displaying the amplified signal to exhibit changes in the physiological characteristics of the person being examined. The invention further comprises apparatus which senses the electromagnetic radiation emitted by a person as a consequence of his physiological response to stress, without bringing a sensor into contact with his body. This information is presented as a composite of heart rate, respiration rate, pulse amplitude and respiratory excursion. The apparatus can also be used to indicate the comparative circulation in different parts of the body, the circulation delay time and information relating to the autonomic nervous response.

The sensor may be placed within a bed, seat cushion or head rest so that the person's physiological response can be measured without his being disturbed by the sensor.

BRIEF DESCRIPTION OF THE DRAWINGS

FIG. 2 is a composite perspective and block diagram of an apparatus for monitoring the physiological characteristics of a subject.

FIG. 7 shows a sensor, pre-amplifier and transmitter for use in the embodiment of FIG. 6a.

DESCRIPTION OF THE PREFERRED EMBODIMENTS

There has long been a need for apparatus that provides basic physiological data on a continuous recorded basis for long-term monitoring requirements from those subjects to which it is impractical or undesirable to attach sensors. This is particularly true of patients suffering burns where it is desirable to have a continuous record of vital signs but electrodes cannot be placed on the skin.

It is well known that biological organisms generate electric fields, the electrocardiogram being an example of this phenomenon. An electric field exists around every nerve fiber and changes when an impulse is "conducted" along the fiber. This field results from the concentration of ions (primarily sodium ions) on one side of the nerve cell membrane. As an impulse moves along the nerve, the membrane suddenly allows the ions to move from one side to the other; and this causes a change in the surrounding electric field.

While the theoretical basis for the operation of the present invention is not fully understood, it is believed to be related to the streaming potential developed in the arteries as a result of the blood flow. According to the Helmholtz double-layer theory, there is a potential difference between the fluid at the wall of a vessel and the fluid at the center of the vessel when the fluid is at rest. The source of this potential is illustrated in FIG. 1.

Figure 1:
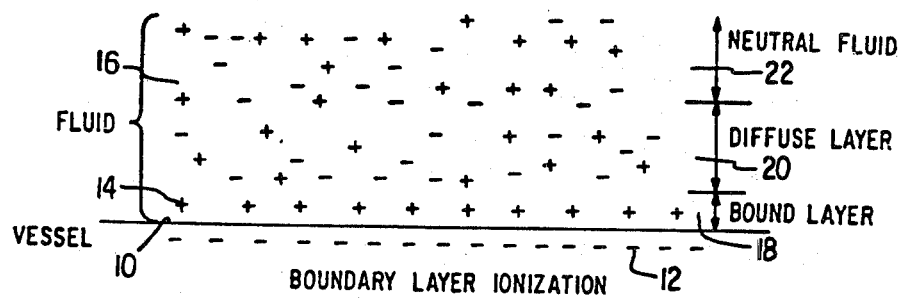
FIG. 1 is a diagram useful in explaining the theory of the invention.

Referring to FIG. 1, the surface of the vessel 10 generally will have some net charge caused either by the orientation of its molecules or by ions absorbed at its surface. Assuming a negative surface charge 12, positive ions 14 in the fluid 16 are attracted to this surface where they form an electrostatically bound layer 18. Since the fluid 16 was initially electrically neutral, this leaves a negative charge in the remainder of the fluid. This negative charge will occur in a diffuse layer 20, and is greatest near the fluid-vessel boundary and diminishes to a neutral state at 22.

The two layers of the Helmholtz double-layer theory are the layer 18 of bound ions near the surface and the oppositely charged diffuse layer 20. Since a separation of charge has occurred, there is a potential difference between the fluid at the wall of the vessel 10 and the fluid in the center of the vessel. This is the "zeta potential," important in fluid electrokinetics.

If the fluid 16 in the vessel is suddenly placed in motion, the diffuse charge layer 20 will move with the fluid. The layer 18 which is nearest the vessel wall is electrostatically bound and will not move. This produces a separation of charge along the direction of fluid motion, resulting in the generation of an electric field outside the vessel 10. The potential drop along the vessel which results from this fluid motion is referred to as a "streaming potential" and has been observed with a variety of fluids in various kinds of vessels. The effect is observed most readily in a fluid with low conductivity such as petroleum products; and in these cases, electric fields of hundreds or even thousands of volts per meter can be generated.

With any given fluid, there are three parameters which affect the magnitude of the streaming potential: (1) the surface charge density at the surface of the vessel; (2) the surface area involved; and (3) the velocity of the fluid. In a blood vessel, there is a large negative surface charge density at the inner wall which is important in connection with the streaming potential. As the main arteries branch into the small arteries in the capillary beds, there is a very large increase in surface area. The blood flow velocity in arteries is of the order of one meter per second at the peak of the pressure curve and this is high enough to produce a streaming potential.

The velocity profile across a section of the blood vessel also has an important effect on the streaming potential. A study of the velocity profile for laminar flow in blood vessels shows that it is quite different from the usual parabolic profile found in the case of steady laminar flow. That is, the oscillatory flow produces a profile which is nearly flat across the diameter with very high shear near the wall of the vessel. Further, there is a close correlation in wave shape between the blood velocity as a function of time and the measurements obtained with the present invention. The present invention measures changes in the streaming potential due to the flow of electrolytes within the bloodstream, and this is accomplished without any direct connection to the physiology.

FIG. 2 is a composite perspective and block diagram of an embodiment of the invention which comprises a flat, flexible sensor 24 having a lower plate 26 which is grounded to minimize interference from 60 Hz electromagnetic fields, an upper plate 28 coupled to a terminal 30 of a pre-amplifier 32, and a middle plate 34 energized by a high voltage power supply 36. Plates 26 and 34 are insulated from each other by a dielectric material 38 and plates 28 and 34 are insulated from each other by a dielectric material 40. An output terminal 42 of pre-amplifier 32 is connected by the central conductor 44 of a coaxial cable 46 to an input terminal 48 of a noise filter 50 having its output terminal 52 coupled to a respiration filter 54 and a pulse filter 56. The outputs of filter 54 and 56 are amplified in amplifiers 58 and 60 respectively, and the amplified signals displayed on a display device 62. The shield 64 of cable 46 is grounded and connected to an input terminal 66 of preamplifier 32 and plate 26 of sensor 24. A low voltage power supply 68 provides excitation power to a terminal 70 of pre-amplifier 32 and to filters 50, 54 and 56, amplifiers 58 and 60 and display device 62.

The area and shape of the sensor plates 26, 28 and 34 is selected in accordance with the part of the body to be examined and the information to be obtained. A small sensor generates a signal of relatively low magnitude but has the advantage that the signal is unique to the point of the body surface which it is near, and therefore to the related underlying physiology. A larger sensor provides a larger signal but represents the conditions over a larger area of the body surface making the information obtained less specific. In some cases, an array of sensors may be used having shapes selected to conform to the particular part of the anatomy and bodily function to be assessed. It has been found that reliable measurements can be obtained with sensor plates as small as 1 inch in diameter, for measurements in the region of the eye, to 8 inch×9 inch rectangular plates used for measurements in the pelvic region. The area and shape of the plates is not critical and may vary widely depending upon the specific application.

The thickness of sensor 24 is greatly exaggerated in FIG. 2 for clarity, the overall thickness of a typical sensor being about 6 mils. Plates 28 and 34 are separated by a dielectric material 40 having a thickness d, and plates 26 and 34 by a dielectric material 38 having a thickness which is at least twice the thickness of the insulation between plates 28 and 34. Typically, plates 26, 28 and 34 are made of copper or aluminum with a thickness of approximately one mil, the thickness of the dielectric material 40 is 1.0 mil or less and the thickness of the dielectric layer 38 about 2.0 mils. Preferably, the thickness of insulating layer 38 between plates 26 and 34 is two to three times the thickness of the insulating layer 40 between the top plate 28 and the middle plate 34. The dielectric layers 38 and 40 are made of an electrically insulating material which may be a polyethylene terephthalate such as Mylar or a polyimide film such as Kapton.

The impedance between sensor plates 26 and 28 is on the order of 100 megohms or more and, in a typical installation, the filters 50, 54 and 56 would for convenience be located about 20 feet from the sensor 24. A shielded cable 46 having an impedance in the range 10,000–15,000 ohms is used to couple the sensor to the noise filter 50, a relatively low impedance cable being used to minimize the amount of noise introduced into the system at the input terminal 48 to filter 50. Since the output of sensor 24 has a high impedance, and the cable 46 is of relatively low impedance, the pre-amplifier 32, which has a gain of about 10, is mounted directly on the sensor 24 and acts as an impedance transformer between the sensor and the cable.

Figure 3:
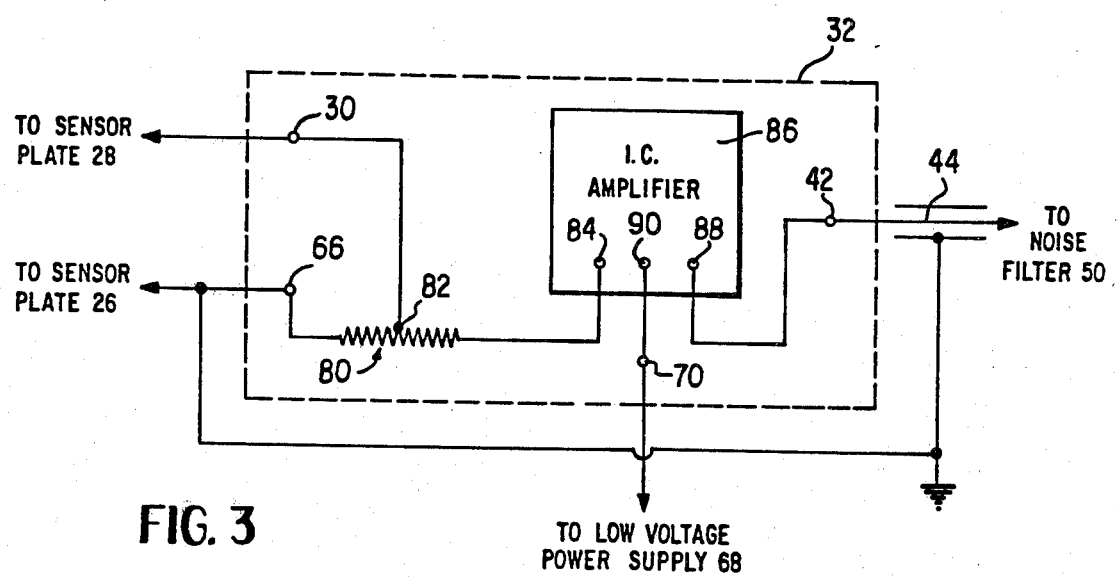
FIG. 3 is a schematic diagram of a pre-amplifier employed in the apparatus of FIG. 2.

As shown in FIG. 3, the pre-amplifier 32 comprises a resistor 80 having a tap 82 connected to the upper sensor plate 28 through terminal 30, one end connected to the grounded lower sensor plate 26 through terminal 66 and the other end connected to a terminal 84 of an integrated circuit FET amplifier 86. A terminal 88 of IC amplifier 86 is coupled through terminal 42 to the central conductor 44 of the coaxial cable 46 and a terminal 90 is coupled to the low voltage power supply 68 through terminal 70. IC amplifier 86 is a type 2N5459 manufactured by Motorola and tapped resistor 80 typically has a value of about 22 megohms.

Noise filter 50 effectively removes those frequencies above 4 Hz including the 60 Hz AC power line fields which saturate the atmosphere and would otherwise interfere with the low frequency fields generated physiologically. The frequencies of greatest interest are below approximately 4 Hz, frequencies in the range up to about 0.5 Hz providing data on respiration and between 0.7 and 1.5 Hz relating to pulse measurements.

Figure 4:
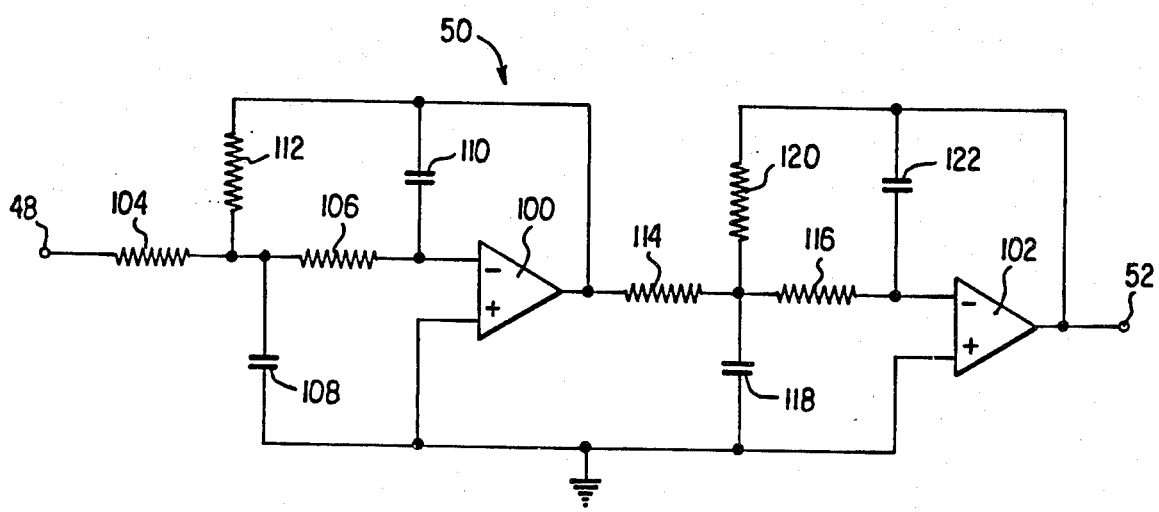
FIG. 4 is a schematic diagram of a typical low pass filter for use in the apparatus of FIG. 2.

A fourth order low pass filter, which may be used for the noise filter, is shown in FIG. 4. This filter comprises two operational amplifiers 100 and 102, the negative input of amplifier 100 being coupled to the center conductor 44 of cable 46 through resistors 104 and 106 which have their junction coupled to ground through a capacitor 108. The output of amplifier 100 is connected to its negative input by a capacitor 110 and to the junction of resistor 104 and 106 by a resistor 112. The positive input terminal of amplifier 100 is grounded.

The output of amplifier 100 is also connected to the negative input of amplifier 102 by resistors 114 and 116 which have their junction connected to ground by a capacitor 118 and to the output of amplifier 102 by a resistor 120. Feedback capacitor 122 is connected between the output of amplifier 102 and its negative input terminal, the positive input terminal of amplifier 102 being grounded.

Typical values for the fourth order low pass noise filter 50 are as follows:

| Operational amplifiers 100, 102-Type 741 manufactured by Motorola: | | |
| --- | --- | --- |
| Resistor | 104 | 10.9K |
| " | 106 | 16.1K |
| " | 112 | 21.8K |
| " | 114 | 4.85K |
| " | 116 | 5.80K |
| " | 120 | 9.70K |
| Capacitors | 108 | 1.0 μF |
| " | 110 | 0.015 μF |
| " | 118 | 1.0 μF |
| " | 122 | 0.2 μF |

Filter 54 is a low pass which transmits frequencies below 0.5 Hz, that is, those frequencies which are of interest in measuring the respiration of a subject. Filter 56 has a pass band in the region 0.7 to 1.5 Hz, and provides information relating to the cardiovascular system of the subject. Filters 54 and 56 are available commercially, being manufactured by Krohn-Hite.

Amplifiers 58 and 60 are of conventional design and each has a gain of about 500 db. They drive an output device 62 which may be any suitable instrument for displaying the generated signal such as a strip chart, cathode ray oscilloscope or bar graph.

The low and high voltage power supplies 68 and 36, respectively, are also of conventional design. The low voltage supply 68 is regulated, but regulation of the high voltage supply is not necessary as it is a special battery generating 180 volts. The high voltage is applied by supply 36 to the middle plate 34 of sensor 24 through a 100 K or 500 K resistor (not shown) to provide a positive charge to the plate with extremely low amperage so that, even if the plate is touched, it does not present a shock hazard. The voltage between plates 34 and 26 is typically in the range 100–180 volts DC.

In operation, the sensor 24 is placed between 3 and 4 inches from the portion of the body of the subject at which the measurement is to be made.

Figure 5A:
FIGS. 5a–5d are time differential strip charts showing the traces obtained when the sensor is placed near the pelvic and head regions of the subject together with an electrocardiogram and a phonocardiogram of the subject.
Figure 5B:
Figure 5C:
Figure 5D:

FIGS. 5a–5d are time traces taken at a paper speed of 100 mm/sec, showing at FIGS. 5a and 5b, the traces obtained on a strip chart used as the output device 62 when the sensor 24 is placed near the pelvic and head regions of the subject, respectively; FIGS. 5c and 5d show, for comparison, an electrocardiogram and a phonocardiogram, respectively, taken on the patient at the same time. This is for comparison of the timing sequences and outputs of various instruments used simultaneously with the non-contact monitor.

In conducting the tests, the subject was supported on a horizontal table with sensors 24 having dimensions of about 8 inches by 9 inches by 0.006 inch placed beneath the covering of the table so that they were spaced from the body of the subject by about three inches.

As can be seen from the traces, the highest amplitude wave of the non-contact monitor appears between the S and T waves on the electrocardiogram and midcycle on the phonocardiogram indicating that the high-amplitude wave observed in FIGS. 5a and 5b represents the main thrust of blood through the major arterial system. Also, by measuring the time required for the major pulse to reach the pelvic area after leaving the head area, the delay times can be measured.

More specifically, the main bolus of blood from the left heart pumping action takes more time to reach the pelvic or leg areas than it does to reach the carotid arteries supplying the head area. Since the recordings are all made simultaneously, a vertical line drawn between FIGS. 5a and 5b demonstrates the difference in time sequence between head and pelvic areas.

An additional test was conducted with sensors placed to obtain separately left and right cranial traces. In each subject, it was found that the amplitude on the left and right sides of the brain were different, sometimes the left being dominant and sometimes the right with no correlation between left and right handedness. Vascular dynamics were checked by palpitation of the carotid pulse which appeared equal on both sides and remained constant over a period of weeks.

Normotensive and known hypertensive subjects were monitored and with considerable consistency the hypertensive patients had higher amplitude waveforms than the normal subjects. Although some correlation was observed between amplitude and the degree of hypertension, the number of tests conducted thus far is too small to show a definite conclusion.

The apparatus, in addition to providing composite measurements of respiration and pulse, can also be used to monitor these quantities simultaneously and independently by the use of separate filters. That is, from one sensor the low frequency spectrum (0–4 Hz) can be split into two bands using filters. The low band then gives information on respiration, and the high band gives information on cardiovascular function.

Figure 6A:
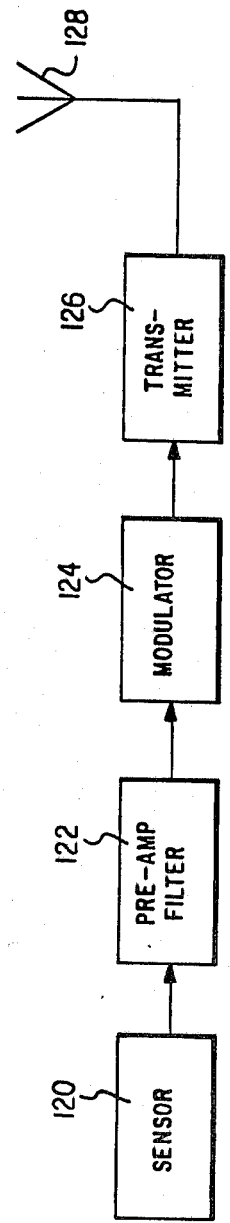
FIGS. 6a and 6b show the transmitter and receiver of another embodiment of the invention which permits remote operation.
Figure 6B:
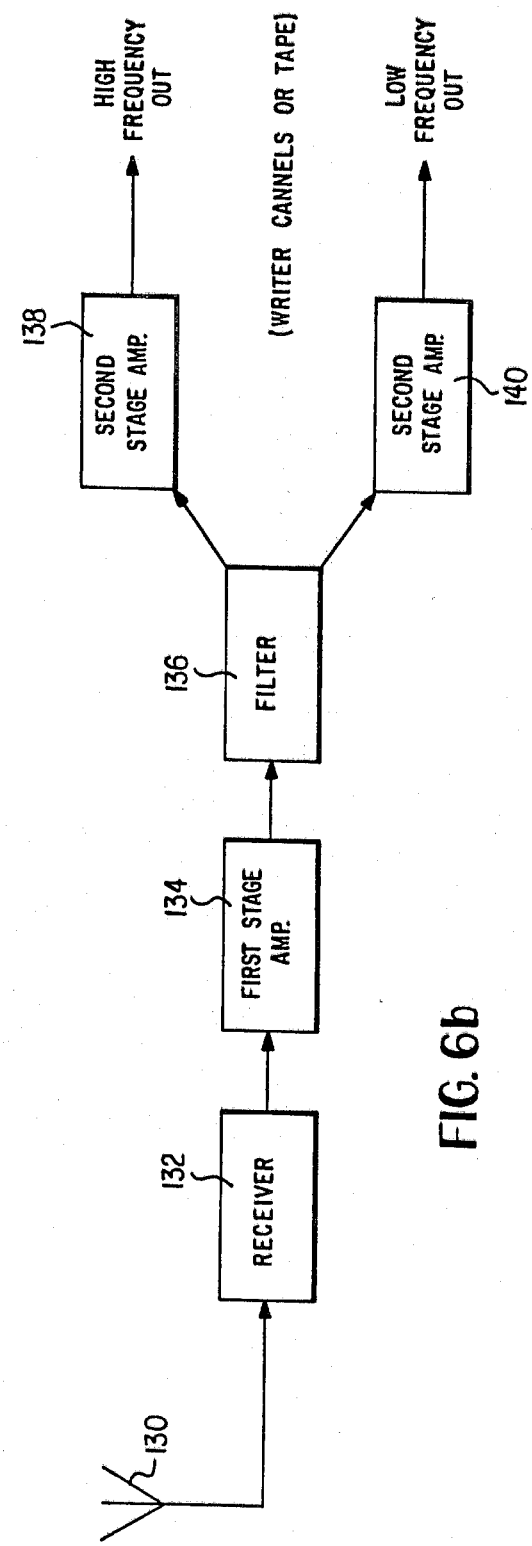

FIGS. 6a and 6b are block diagrams of a transmitter and a receiver, respectively, for a system that provides remote sensing to a central data reduction center for processing physiological information from a subject not restrained by a wiring harness. This is particularly useful when it is desirable to monitor an individual over an extended period of time during which he can remain mobile and not be restricted to a single location.

Referring to FIG. 6a, the sensor 120, which may be similar in construction to sensor 24, is carried by the subject together with a combined pre-amplifier and low pass filter 122, modulator 124, transmitter 126 and transmitting antenna 128. At the receiver terminal, an antenna 130 receives the signal transmitted by antenna 128 and couples it through a receiver 132 and first stage amplifier 134 to a filter circuit 136 which separates the received signal into a component having frequencies below 0.5 Hz for measuring respiration and a component having frequencies in the range 0.7 to 1.5 Hz for making pulse measurements. In addition, if necessary, a noise filter similar to filter 50 shown in FIGS. 2 and 4 may be interposed between filter 136 and amplifier 134 or made a part of filter circuit 136. The 0.7 to 1.5 Hz output from filter 136 is amplified in a second stage amplifier 140. The 0.0–0.5 Hz output from filter 136 is amplified in a second stage amplifier 138. The signals are displayed as disclosed in connection with the embodiment of FIG. 2.

Figure 7:
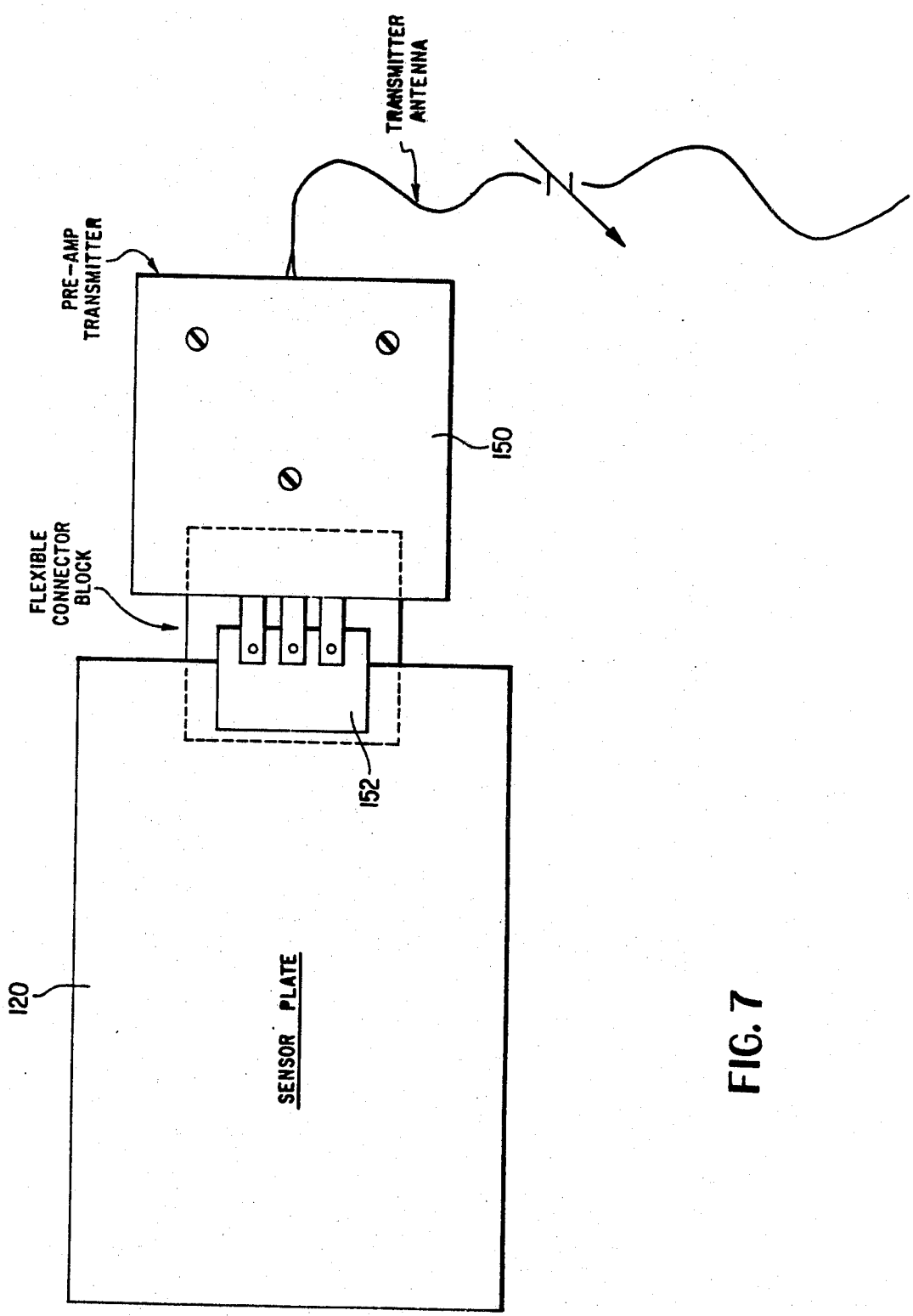

FIG. 7 shows an embodiment of the circuit of FIG. 6 wherein the pre-amplifier filter 122, modulator 124 and transmitter 126 are combined in a commercially available integrated circuit 150 manufactured by Motorola and other electronic firms. Integrated circuit 150 is attached directly to the sensor plate 120 by means of a flexible connector block 152.

It will be understood that the above description of the present invention is susceptible to various modifications, changes and adaptations, and the same are intended to be comprehended within the meaning and range of equivalents of the appended claims.

What is claimed is:

1. A method of monitoring the phsiological characteristics of a subject by measuring changes in the streaming potential caused by the flow of electrolytes within the blood stream of said subject, said method comprising the steps of
    placing sensor means for measuring said streaming potential adjacent to and spaced from the body of said subject;
    generating a sensor output signal corresponding to said streaming potential, said streaming potential being determined by the physiological responses of said subject;
    filtering said sensor output signal to provide a filter output signal having frequency components not higher than 4 Hz; and
    displaying said filter output signal, the displayed signal corresponding to changes in said streaming potential and being indicative of the physiological characteristics of said subject.

2. The method defined by claim 1 wherein said filtering step further includes separating said filter output signal into first and second frequency components, said first component being below 0.5 and related to the respiration of said subject and said second component being between 0.7 and 1.5 Hz and related to the cardiovascular system of said subject.

3. Apparatus for monitoring the physiological characteristics of a subject by measuring changes in the streaming potential caused by the flow of electrolytes within the bloodstream of said subject, comprising
    at least one sensor means for generating a sensor output signal corresponding to said streaming potential, said sensor means being positionable near but not in contact with the body of said subject;
    filtering means coupled to the output of said sensor means, said filtering means providing a filter output signal having frequency components not higher than 4 Hz; and
    display means coupled to the output of said filtering means, said display means providing a signal corresponding to changes in said streaming potential and being indicative of the physiological characteristics of said subject.

4. Apparatus as defined in claim 3 which further comprises additional filtering means coupled between said filtering means and said display means, said additional filtering means separating said filter output signal into first and second frequency components, said first component being below 0.5 Hz and related to the respiration of said subject and said second component being between 0.7 and 1.5 Hz and related to the cardiovascular system of said subject.

5. Apparatus as defined in claim 3 or 4 wherein said filtering means is a fourth order low pass filter.

6. Apparatus as defined in claim 3 or 4 wherein said sensor means comprises first, second and third spaced parallel conductive plates, said second plate being interposed between said first and third plates; dielectric material separating said first plate from said second plate and said second plate from said third plate; means grounding said third plate; means coupling said second plate to a voltage source having a predetermined magnitude and means coupling said first plate to the input of said filtering means.

7. Apparatus as defined in claim 6 wherein the thickness of the dielectric material separating said second plate from said third plate is more than twice the thickness of the dielectric material separating said first plate from said second plate.

* * * * *